(12) United States Patent
Wirtz

(10) Patent No.: US 9,683,229 B2
(45) Date of Patent: Jun. 20, 2017

(54) MATRIX AND METHOD FOR PURIFYING AND/OR ISOLATING NUCLEIC ACIDS

(71) Applicant: Ralph Markus Wirtz, Cologne (DE)

(72) Inventor: Ralph Markus Wirtz, Cologne (DE)

( * ) Notice: Subject to any disclaimer, the term of this patent is extended or adjusted under 35 U.S.C. 154(b) by 0 days.

(21) Appl. No.: 14/166,759

(22) Filed: Jan. 28, 2014

(65) Prior Publication Data

US 2014/0221638 A1    Aug. 7, 2014

Related U.S. Application Data

(63) Continuation of application No. PCT/EP2012/065574, filed on Aug. 9, 2012.

(51) Int. Cl.
| | |
|---|---|
| *C07H 21/00* | (2006.01) |
| *C01G 49/08* | (2006.01) |
| *C04B 35/26* | (2006.01) |
| *C04B 35/64* | (2006.01) |
| *C12N 15/10* | (2006.01) |

(52) U.S. Cl.
CPC ....... *C12N 15/101* (2013.01); *C12N 15/1006* (2013.01)

(58) Field of Classification Search
CPC .............. C12N 15/1006; C12N 15/101; C12Q 2563/137; C12Q 2563/143; C12Q 2563/155
See application file for complete search history.

(56) References Cited

U.S. PATENT DOCUMENTS

| | | | |
|---|---|---|---|
| 6,255,477 B1 * | 7/2001 | Kleiber et al. ............... | 536/25.4 |
| 6,870,047 B2 * | 3/2005 | Kleiber et al. ............... | 536/25.4 |
| 7,371,830 B2 * | 5/2008 | Kleiber et al. ............... | 530/412 |
| 7,964,380 B2 * | 6/2011 | Utermohlen et al. ........ | 435/177 |
| 8,129,118 B2 * | 3/2012 | Weindel et al. ............. | 435/6.12 |
| 8,206,990 B2 * | 6/2012 | Ritt et al. ......................... | 436/94 |
| 8,288,169 B2 * | 10/2012 | Utermohlen et al. ........ | 436/177 |
| 8,460,941 B2 * | 6/2013 | Ritt et al. ......................... | 436/94 |
| 8,481,017 B2 * | 7/2013 | Schlenoff et al. ......... | 424/78.08 |
| 8,759,053 B2 * | 6/2014 | Phelps et al. ................. | 435/168 |
| 8,906,831 B2 * | 12/2014 | Eid et al. ........................ | 506/16 |
| 8,945,912 B2 * | 2/2015 | Bashir et al. .............. | 435/287.2 |
| 2007/0178308 A1 | 8/2007 | Furusawa et al. ............ | 428/403 |

FOREIGN PATENT DOCUMENTS

| | | |
|---|---|---|
| DE | 101 03 652 A1 * | 8/2002 |
| DE | 10103652 | 8/2002 |
| WO | WO 2008/043551 | 4/2008 |
| WO | WO 2009/102258 | 8/2009 |
| WO | WO 2010/093793 | 8/2010 |
| WO | WO 2012/116945 | 9/2012 |

OTHER PUBLICATIONS

Trudel, S., "Unexpected Magnetism in Gold Nanostructures: Making Gold Even More Attractive," Gold Bulletin, 44(1), 3-13 (Feb. 1, 2011).*
Berensmeier, S., "Magnetic Particles for the Separation and Purification of Nucleic Acids", Applied Microbiology and Biotechnology, vol. 73, Issue 3, pp. 495-504, (Dec. 2006). Abstract only.
Boom, R., et al., "Rapid and Simple Method for Purification of Nucleic Acids", Journal of Clinical Microbiology, vol. 28, No. 3, pp. 495-503, (May 1990).
European Official Action issued in a corresponding foreign application, pp. 1-4 (Sep. 4, 2015).

\* cited by examiner

*Primary Examiner* — Lawrence E Crane

(74) *Attorney, Agent, or Firm* — J. Peter Paredes; David G. Rosenbaum; Rosenbaum IP, P.C.

(57) ABSTRACT

The present invention relates to matrix materials suitable for use in purifying and/or isolating nucleic acids from a biological sample, which matrix comprises a surface comprising at least one element selected from the group consisting of Germanium, Tin and/or Lead, or at least one salt thereof, and methods related therewith.

16 Claims, 3 Drawing Sheets

MATRIX AND METHOD FOR PURIFYING AND/OR ISOLATING NUCLEIC ACIDS

CROSS-REFERENCE TO RELATED APPLICATIONS

The present application claims priority from and is a continuation from PCT Application No. PCT/EP2012/065574, filed Aug. 9, 2012; which claims priority from Patent Application No. GB 1113698.3, filed Aug. 9, 2011, all of which are herein incorporated by reference in their entireties.

BACKGROUND

The present invention is related to a matrix and a method for purifying and/or isolating nucleic acids.

The purification and isolation of nucleic acids from biological samples is a key technology in molecular diagnostics, epidemiology, food analytics, forensics and biological science. One of the most popular approaches involves binding of nucleic acids to silica surfaces in the presence of chaotropic agents. The principles of this approach are for example described by Boom et al (1990), J. Clin. Microbiol. 1990 March; 28(3): 495-503. Kits utilizing this technology are for example marketed by BioMerieux, Qiagen or Promega.

Nucleic acids dissolved in a liquid sample have the ability to bind silica, i.e., amorphous $SiO_2$, in the presence of high concentrations of chaotropic salts ("binding buffer"). The latter denature biomolecules by disrupting the hydration shell surrounding them. This allows positively charged (e.g., sodium ions provided with the binding buffer) ions to form a salt bridge between the negatively charged silica and the negatively charged DNA backbone. In a next step, a low ionic strength buffer ("low salt buffer") is being used to disrupt theses bindings by solubilizing the nucleic acids, in order to elute the nucleic acids.

SUMMARY OF THE INVENTION

Provided herein are systems, methods and compositions for a matrix material suitable for use in purifying and/or isolating nucleic acids from a biological sample, wherein the matrix material comprises a surface comprising at least one element selected from the group consisting of Germanium, Tin and/or Lead, or at least one salt thereof.

The methods, systems, and compositions are set forth in part in the description which follows, and in part will be obvious from the description, or can be learned by practice of the methods, compositions, and systems. The advantages of the methods, compositions, and systems will be realized and attained by means of the elements and combinations particularly pointed out in the appended claims. It is to be understood that both the foregoing general description and the following detailed description are exemplary and explanatory only and are not restrictive of the methods, compositions, and systems, as claimed.

BRIEF DESCRIPTION OF THE DRAWINGS

Additional details, features, characteristics and advantages of the object of the invention are disclosed in the claims, and the following description of the respective figures and examples, which, in an exemplary fashion, show preferred embodiments of the present invention. However, these drawings should by no means be understood as to limit the scope of the invention.

DETAILED DESCRIPTION OF THE INVENTION

Figure 1:
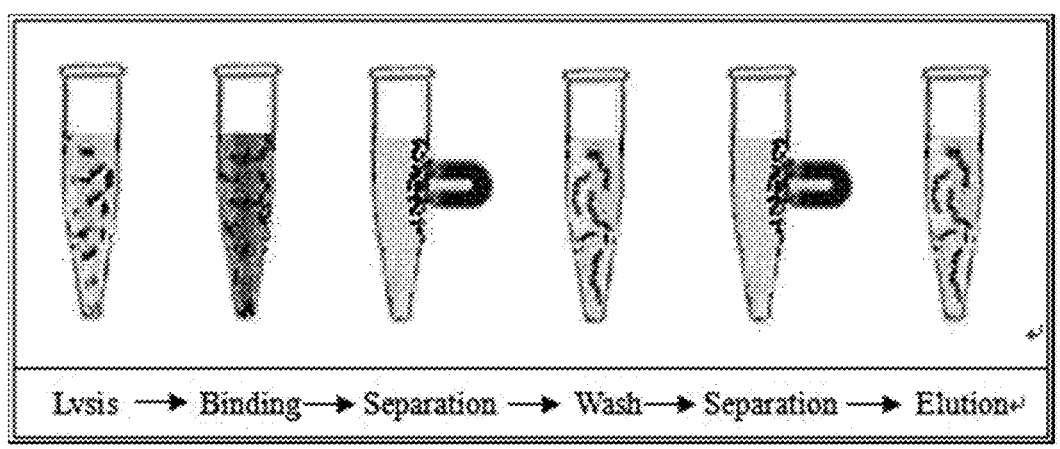
FIG. 1 shows a schematic view of the method according to the invention.
Figure 2:
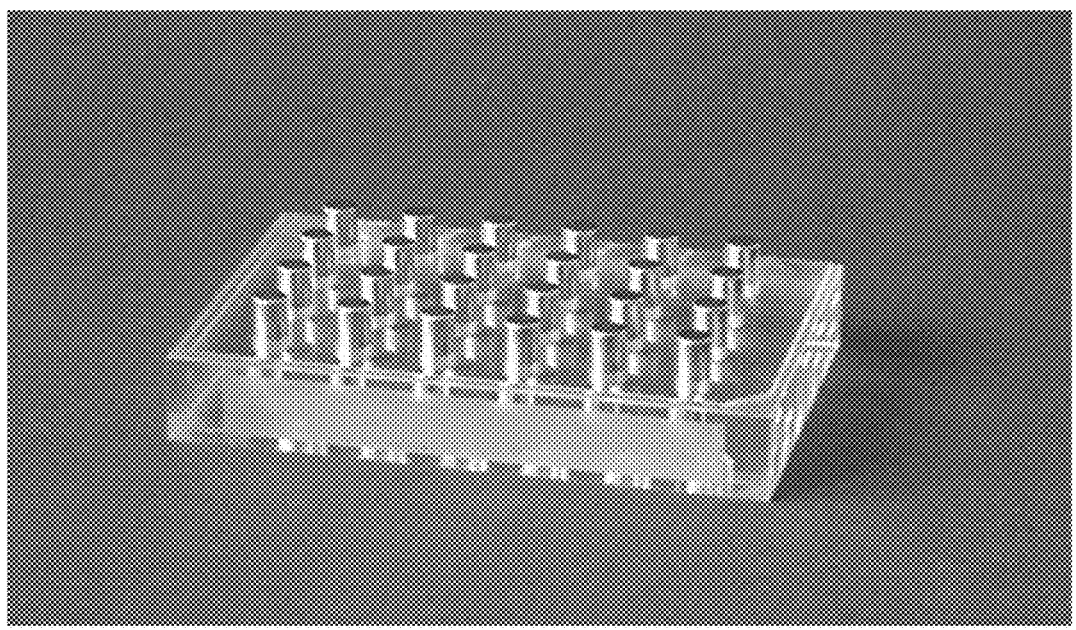
FIG. 2 shows a magnetic separator as can be sued in the context of the present invention FIG. 3 demonstrates the binding principle between $GeO_2$ coated surfaces and nucleic acids.
Figure 3:
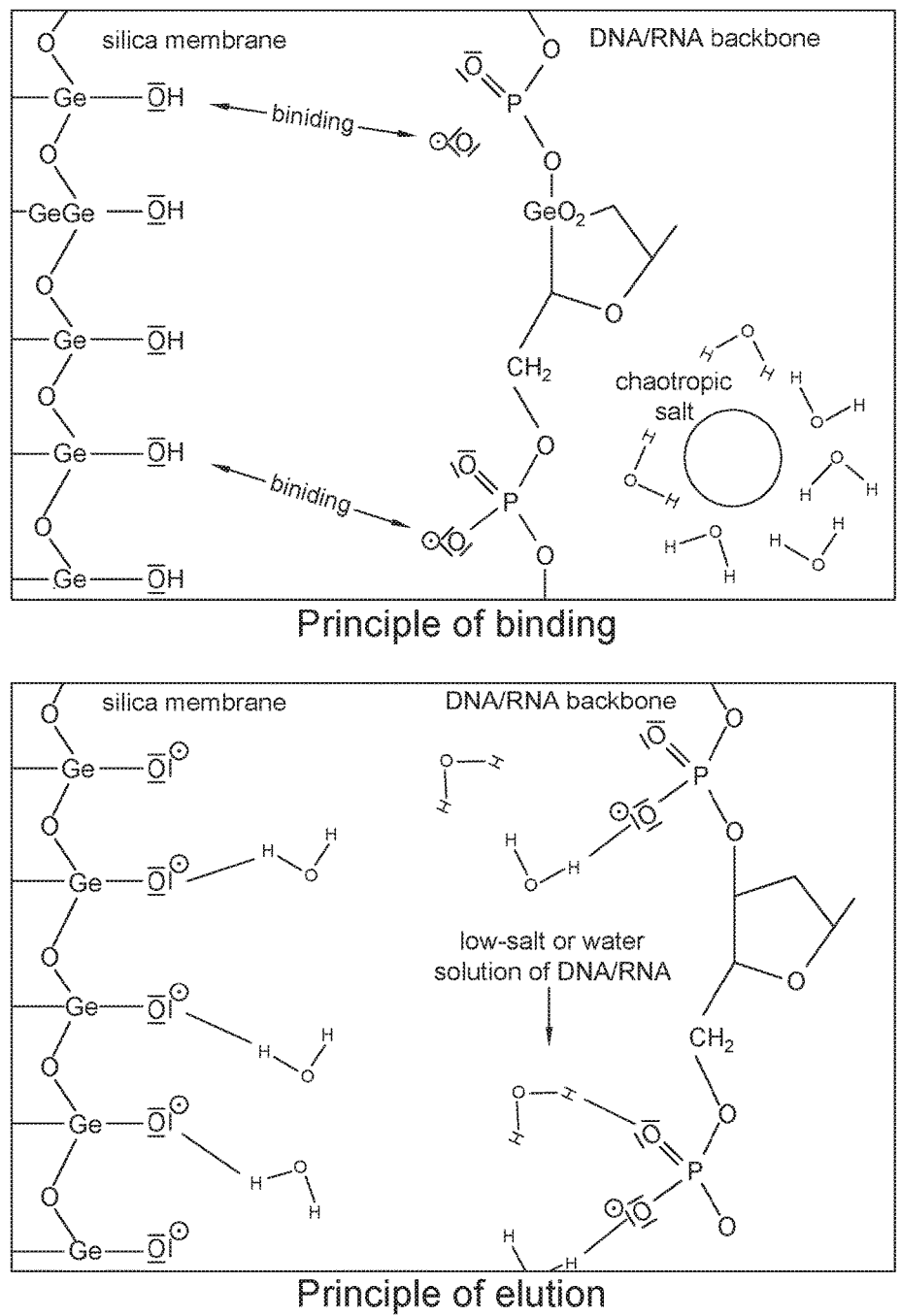

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

The dependent claims are related to preferred embodiments. It is yet to be understood that value ranges delimited by numerical values are to be understood to include the said delimiting values.

According to the invention, a matrix material suitable for use in purifying and/or isolating nucleic acids from a biological sample is provided, which matrix comprises a surface comprising at least one element selected from the group consisting of Germanium, Tin and/or Lead; or at least one salt thereof.

Germanium (Ge), Tin (Sn) and Lead (Pb) belong to the Carbon Group in the periodic table, also called group 14 according to the new IUPAC system. Compared to the remaining elements in the Carbon Group, i.e., Carbon (C) and Silicon (Si), the three former elements have in common a high density and atomic mass, plus a good electrical conductivity, which seperates them from Silicon and Carbon. Germanium (Ge), Tin (Sn) and Lead (Pb) thus form a subgroup with group 14. The following table 1 shows this clearly:

TABLE 1

| element | atomic mass | density ($kg/m^3$) | electrical conductivity (S/m) |
|---|---|---|---|
| Carbon | 12.011 | 2250-3510 | $1 \times 10^{-4}$-$3 \times 10^6$ |
| Silicon | 28.086 | 2330 | $2.52 \times 10^{-4}$ |
| Germanium | 72.59 | 5323 | 1.45 |
| Tin | 118.71 | 7310 | $9.17 \times 10^6$ |
| Lead | 207.2 | 11340 | $4.81 \times 10^6$ |

Furthermore, Germanium, Tin and Lead have a greater ionic diameter than Silicon. All these technical features contribute to significant differences in the binding reaction of Silicon, on the one hand side, and Germanium, Tin and Lead, on the other hand side, with the nucleic acid backbone.

In a preferred embodiment, said matrix comprises Germanium or a Germanium salt, preferably Germanium oxide.

Germanium a chemical element with the symbol Ge and atomic number 32. Germanium dioxide ($GeO_2$), also called Germanium Oxide (in contrast to Germanium monoxide, which is GeO) or "Germania", is an inorganic compound, an oxide of Germanium. Its chemical formula is $GeO_2$. Other names include germanic acid, G-15, and ACC10380. It forms as a passivation layer on pure Germanium in contact with atmospheric oxygen. The forms of Germanium dioxide parallel, to an extent, those of silicon dioxide.

Hexagonal $GeO_2$ has the same structure as β-quartz (Germanium having coordination number 4); tetragonal $GeO_2$ (the mineral argutite) has the rutile-like structure of stishovite (Germanium having coordination number 6); and amorphous (glassy) $GeO_2$ is similar to fused silica. Germanium dioxide can be prepared in both crystalline and amorphous forms. Like Silica, it can be provided in a gel form, which is a granular, vitreous, highly porous form which, despite its name, is a solid having a large inner surface with pores in the nanometer range.

Because Germanium has a higher electronegativity than Silicon (2.02 vs 1.74), liquid-based deposition processes of, e.g., $GeO_2$ on metal surfaces have a higher efficiency than with $SiO_2$. Further, due to that higher electronegativity the binding reaction between $GeO_2$ and nucleic acids is stronger, because the $GeO_2$-domains have a higher polarity.

Generally, the matrix material can consist entirely of Germanium oxide. In a preferred embodiment, however, only the surface of the material comprising Germanium oxide, while the core areas of the material comprises other materials. Such embodiment can be used to add, to the nucleic acid binding capacity of Germanium oxide, other technical features which can be useful in the present context. Further, this opens up the possibility to use cheaper materials than Germanium, or its derivatives, in the core areas.

In a preferred embodiment of the present invention, it is provided that said matrix material is provided in at least one shape selected from the group consisting of: Reaction vessel coating, Particles, Powder, Fibres, and Membrane.

In case the matrix material is a membrane, such membrane can for example be used in a spin column, e.g., in column-based nucleic acid purification. In case the matrix material is in form of particles, the latter can be used in particle-based nucleic acid purification systems. In case the matrix material is in form of a reaction vessel coating, nucleic acids can be bound the walls of a reaction vessel for purification purposes. In case the matrix material is in form of fibres, a wool-like material can be produced which can be used in columns for nucleic acid purification. In case the matrix material is in form of powder, a suspension can be produced similar to glass milk, which has a greater surface area, and thus can bind more nucleic acids per unit volume than other regularly shaped silica matrices.

In another preferred embodiment of the present invention, it is provided that said particles have at least one feature selected from the group of: Spherical shape, and a Diameter between ≥0.01 μm and ≤100 μm.

As used herein, the term "spherical shape" is not always required to be a true sphere or a nearly true sphere because the purpose is to compare it with such longitudinal shapes (like in fibres) or planar shapes (like in membranes). Such type of particles is also called "beads", or nano- or microspheres.

Preferably, the mean diameter of the said particles is in the range of ≥0.05 μm and ≤5 μm, even more preferred in the range of ≥0.1 μm and ≤1 μm. Particularly preferred, the mean diameter is in the range of ≥0.15 μm and ≤0.25 μm.

In another preferred embodiment of the present invention, it is provided that said material is, at least in part, magnetically-responsive.

The term "magnetically responsive material" refers to any magnetic, paramagnetic or magnetizable material, The term also refers to the capacity of a material to migrate, relative to under the influence of a magnetic field.

In such embodiment, a magnet can be used to collect the matrix material, e.g., the beads, after they have bound the nucleic acids. In this embodiment, washing steps or elution steps are facilitated, particularly when Formalin Fixed Paraffin Embedded (FFPE) sample material is used (see below).

Preferably, the matrix material comprises, or consists, at least in part, of, an inorganic material. It is particularly preferred that matrix material comprises a magnetic or paramagnetic material selected from the group consisting of: Iron oxide, Magnetic polymers, and Gold.

Iron oxide particles are for example commercially available as toner for photocopiers. These particles are produced under very high standards and have thus a very even size distribution, are chemically and have a high purity. Such type of particles, although witn a silkica coating, are for example marketed by Mobitec, Goettingen, Del. Alternatively, said iron oxide particles consist of hydrophilic $Fe_3O_4$, which is for example available as BAYOXIDE E8706, E8707, E8709 and/or E8710. As regards the somehow surprising feature that Gold can have magnetic properties, reference is made to Trudel (2011), Unexpected magnetism in gold nanostructures: making gold even more attractive Gold Bulletin Volume 44, Number 1, 3-13.

In magnetic polymer beads, the particle matrix consists of either latex, polystyrene or silica with, e.g., homogeneously incorporated nanometer-sized iron oxide. Such type of beads is for example marketed as Dynabeads by life technologies.

In a particularly preferred embodiment, magnetically responsive beads with, e.g., an iron oxide core and a Germanium dioxide coating are being used. According to another aspect of the invention, a method for purifying and/or isolating nucleic acids from a biological sample is provided, in which method a matrix material according to the invention is used.

In a preferred embodiment of said method, the nucleic acids to be purified and/or isolated are selected from the group consisting of DNA and or RNA. It is particularly preferred that the nucleic acids are genomic DNA, mRNA, and/or microRNA.

In a particularly preferred embodiment of said method, the biological sample is at least one selected from the group consisting of: Fresh tissue samples, Frozen tissue samples, Fixed tissue samples, Forensic or paleontologic samples, Samples obtained from feces, dried biological material, mummies, taxidermized organisms, Food samples, and/or Plant samples For fixed tissue samples, at least one fixative may be used in a preferred embodiment which is selected from the group consisting of Neutral Buffered Formaline, Unbuffered Formaline, Glutaraldehyde, Ethanol, Acetone, Methanol, Methacarn, Carnoy's fixative, AFA-Fixative (Formaldehyde, Ethanol and acetic acid), Pen-Fix (alcoholic formalin fixative), Glyo-Fixx (glyoxal-based fixative), Hope (Hepesglutamic acid buffer mediated organic solvent fixative), and/or Zinc Formal-Fixx (Formaldehyde fixative which contains zinc).

A preferred type of fixed tissue samples are Formalin Fixed Paraffin Embedded (FFPE) tissue samples. Routinely, in tumor diagnosis tissue samples are taken as biopsies form a patient and undergo diagnostic procedures. For this purpose, the samples are fixed in formaline, embedded in paraffine and are then examined with immunohistochemistry methods. The formaline treatment leads to the inactivation of enzymes, as for example the ubiquitous RNA-digesting enzymes (RNAses). For this reason, the mRNA status of the tissue (the so called transcriptome), remains unaffected.

However, molecular analysis in FFPE samples, particularly by means of nucleic acid amplification and detection, is a difficult manner because the fixation process crosslinks proteins and nucleic acids. Further, the process to dissolve nucleic acids from FFPE tissue which is usually done manually is highly error-prone. Another issue is that in FFPE samples, nucleic acids are often disrupted into very short fragments, which, although they are still long enough to be analyzed by PCR, pose problems when being isolated with standard means.

Such samples can successfully be treated with a preferred embodiment of the invention, in which magnetically responsive beads with, e.g., an iron oxide core and a Germanium dioxide coating are used. Because being magnetic the said beads can be used in an automatic environment, thus eliminating the errors caused by manual dissolving of nucleic acids from FFPE tissue. Further the beads can bind also small fragments of nucleic acids.

Regardless from the way the sample has been conserved, the sample type may comprise tissue sections, Tissue Micro Array cores, samples from needle aspirates, smear samples, microdissected samples, and samples obtained from cell culture.

In another preferred embodiment of said method, the nucleic acids are purified and/or isolated in the presence of a chaotropic agent.

The term "chaotropic agent" as used herein refers to salts of particular ions which, when present in a sufficiently high concentration in an aqueous solution, cause proteins present therein to unfold and nucleic acids to loose secondary structure. It is thought that chaotropic ions have these effects because they disrupt hydrogen-bonding networks that exist in liquid water and thereby make denatured proteins and nucleic acids thermodynamically more stable than their correctly folded or structured counterparts.

In yet another preferred embodiment of said method, the purification and/or isolation comprises a step of focusing a magnetically responsive matrix material according to the invention by means of a magnetic field.

In this embodiment, washing steps following the binding of nucleic acids are facilitated, because the matrix material with the nucleic acids can be immobilized temporarily, thus avoiding that they are washed away and thus get lost.

According to another aspect of the invention, a kit of parts suitable for use in a method according to the invention is provided, said kit comprising a chaotropic agent and, optionally, a matrix material according to the invention.

Preferably, said kit further comprises a binding buffer and a low salt buffer.

As low salt buffer, TE buffer or water are preferably used. TE buffer is a commonly used buffer solution in molecular biology, especially in procedures involving DNA or RNA. "TE" is derived from its components Tris, a common pH buffer, and EDTA, a molecule that chelates cations like $Mg^{2+}$. A typical recipe for making 10:1 TE buffer is 10 mM Tris, (ad pH 8.0 with HCl) and 1 mM EDTA The binding buffer comprises a chaotropic agent and a buffer, plus, optionally, a detergent and/or NaCl and/or KCl can be added in high concentrations. In the latter case, the buffer is also called high salt buffer.

The Kit or method according to the invention preferably comprises at least one chaotropic agent selected from the group consisting of: Urea, Thiourea, Guanidinium chloride, Guanidinium hydrochloride, Thiocyanates, like Guanidinium thiocyanate, Perchlorates, like Lithium perchlorate or sodium perchlorate, Trichloracetates, like sodium trichloroacetate, Iodides, like sodium iodide, and Barium salts.

Urea is preferably used in a concentration of 6-8 mol/l. Thiourea is preferably used in a concentration of 2 mol/l. Guanidinium chloride is preferably used in a concentration of 6 mol/l. Lithium perchlorate is preferably used in a concentration of 4.5 mol/l.

Preferably, said kit or method further comprises at least one agent selected from the group consisting of: Degrading enzyme, Detergent, and Alcohol.

Degrading enzymes include Proteases. Proteinase K is one of these, and actually works very well in these denaturing buffers; the more denatured the protein, the better Proteinase K works. Lysozyme, however, does not work in the denaturing and so lysozyme treatment is usually done before adding the denaturing salts. Detergents help with protein solubilization and lysis. Preferably, Triton X 100 is used as detergent. Alcohol is used to enhance and influence the binding of nucleic acids to the matrix, and for washing purposes. Preferably, ethanol and/or isopropanol are used In a preferred embodiment, the kit according to the invention further comprises a magnetic separator. In this embodiment, washing steps following the binding of nucleic acids are facilitated, because the matrix material with the nucleic acids can be immobilized temporarily, thus avoiding that they are washed away and thus get lost. Such magnetic separator can preferably be embodied in the form of a microtiter plate which can accommodate a number of micro reaction vessels, like Eppendorf tubes. Said separator may consist of a tablet, or a block, e.g., from Plexiglas, with a number of wells (either for the samples themselves, or for accommodation of the Eppendorf tubes). In the lower section of the tablet, or block, one or more magnets (either permanent magnets or electromagnets) are disposed, which attract the magnetically responsive matrix materials, e.g. the $GeO_2$ coated iron oxide beads.

Alternatively, said magnetic separator can consist of an individual tablet, or block, having the size of a micotiter plate, in which one or more magnets are disposed, which block can then be used together with a microtiter plate in a sandwich configuration. A standard size of such magnetic separator is 12.8 cm×8.6 cm×2.8 cm for use with standard 96 well microtiter plates.

According to yet another aspect of the invention, the use of a kit, method or matrix according to the invention for at least one purpose selected from the group consisting of: Forensics, Molecular diagnostics, Food analytics, and/or Plant analytics is provided.

EXAMPLES

1. Production of a Matrix Material According to the Invention $Na_2GeO_3$ is produced by reaction of Sodium carbonate and Germanium dioxide when molten according to the following scheme (1):

$$Na_2CO_3 + GeO_2 \rightarrow Na_2GeO_3 + CO_2 \qquad (1)$$

Anhydrous $Na_2GeO_3$ contains a chain polymeric anion composed of corner shared $\{GeO_4\}$ tetrahedral, and not a discrete $GeO_3^{2-}$ ion.

50 g of iron oxide particles as used for toner are given into 1000 ml of an aqueous 0.25% solution of $Na_2GeO_3$. After stirring for an hour, the particles are filtered off, washed subsequently with water and ethanol, and are then dried. Alternatively, a 20% solution of $Na_2GeO_3$ can be used.

Other ways to created GeO$_2$-coated matrix material comprise Plasma Enhanced Chemical Vapor Deposition and Chemical Vapor Deposition.

2. A Nucleic Acid Purification Kit According to the Invention.

A non-limiting example of a nucleic acid purification kit according to the invention comprises at least the following items:

Binding buffer (500 μl): 5 M Guanidiniumisothiocyanate, 10 mM TrisHCl, 20% Triton, pH 8.8 Optionally, a NaCl and/or KCl can be added in high concentrations;

Washing buffer: 50 vol % ethanol, 20 mM NaCl, 10 mM Tris-HCl, pH 7.5;

Low salt buffer (50 μl): 50 μl TE-buffer (10 mM Tris, 1 mM EDTA, pH 7.0);

GeO$_2$ coated particles (optional): 3 mg.

3. Purification of a ESR1 Nucleic Acid with a Matrix Material According to the Invention, and Further Amplification RNA is isolated from formalin-fixed paraffin-embedded ("FFPE") tumor tissue slice samples. The FFPE slices are lysed and treated with Proteinase K for 2 hours 55° C. with shaking After adding a binding buffer (high salt+chaotropic salts) and GeO$_2$-coated magnetic particles nucleic acids are bound to the particles within 15 minutes at room temperature. On a magnetic stand the supernatant is taken away and beads are washed several times with washing buffer. After adding elution buffer (low salt) and incubating for 10 min at 70° C. the supernatant is taken away on a magnetic stand without touching the beads.

After normal DNAse I treatment for 30 min at 37° C. and inactivation of DNAse I the solution is used for reverse transcription-polymerase chain reaction (RT-PCR). RT-PCR is run as standard kinetic one-step Reverse Transcriptase TaqMan™ polymerase chain reaction (RT-PCR) analysis on a ABI7900 (Applied Biosystems) PCR system for assessment of mRNA expression.

Raw data of the RT-PCR are normalized to one a housekeeping gene according to standard methods.

Experiments shown that the determination of ESR1 by RT PCR consistently yields better results than analysis by immunohistochemistry (IHC).

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A matrix material comprising a surface only covered by germanium oxide, or at least one salt thereof, wherein said matrix material is non-covalently bound to said germanium oxide.

2. The matrix material according to claim 1, wherein said matrix material is provided in at least one shape which is selected from the group consisting of: reaction vessel coating, particles, powder, fibres, and membrane.

3. The matrix material according to claim 2, wherein said particles have at least one feature selected from the group of: spherical shape, and diameter between ≥0.01 μm and ≤100 μm.

4. The matrix material according to claim 1, further comprising wherein said material is, at least in part, magnetically-responsive, and wherein said magnetically responsive matrix material comprises a magnetic or paramagnetic material selected from the group consisting of: iron oxide, iron oxide particles, and magnetic polymers.

5. The matrix material according to claim 4, further comprising wherein said material is an inorganic material.

6. The matrix material according to claim 1, wherein the matrix material further comprises of iron oxide.

7. A method for purifying and/or isolating nucleic acids from a biological sample, which method comprises the following steps: binding a matrix material according to claim 1 to the nucleic acids, washing the nucleic acid-bond matrix material, and eluting the nucleic acids from the matrix material.

8. The method according to claim 7, wherein the nucleic acids to be purified and/or isolated are selected from the group consisting of: RNAs.

9. The method according to claim 8, wherein the biological sample is at least one selected from the group consisting of: fresh tissue samples, frozen tissue samples, fixed tissue samples, forensic or paleontologic samples, samples obtained from feces, dried biological material, mummies, taxidermized organisms, food samples, and plant samples.

10. The method according to claim 9, further comprising wherein the nucleic acids are purified and/or isolated in the presence of a chaotropic agent.

11. The method according to claim 10, further comprising wherein the purification and/or isolation comprises a step of focusing a magnetically responsive matrix material by means of a magnetic field.

12. A kit suitable for purifying and/or isolating nucleic acids from a biological sample, said kit comprising: a chaotropic agent and a matrix material as defined in claim 1.

13. The kit according to claim 12, wherein said kit further comprises a binding buffer and a low salt buffer.

14. The kit according to claim 13, wherein the chaotropic agent is at least one selected from the group consisting of: urea, thiourea, guanidinium hydrochloride, guanidinium thiocyanate, lithium percholorate, sodium perchlorate, sodium trichloroacetate, sodium iodide, and barium salts.

15. The kit according to claim 14, said kit further comprising a magnetic separator.

16. The kit according to claim 15, wherein the kit further comprises at least one agent selected from the group consisting of: degrading enzyme, detergent, and alcohol.

* * * * *